United States Patent [19]

Stoudt et al.

[11] 4,235,994

[45] Nov. 25, 1980

[54] HIGH MOLECULAR WEIGHT MENINGOCOCCAL GROUP C VACCINE AND METHOD FOR PREPARATION THEREOF

[75] Inventors: Thomas H. Stoudt, Westfield; Dennis J. Carlo, South Amboy; Arpi Hagopian, Clark, all of N.J.

[73] Assignee: Merck & Co., Inc., Rahway, N.J.

[21] Appl. No.: 919,359

[22] Filed: Jun. 26, 1978

Related U.S. Application Data

[62] Division of Ser. No. 820,665, Aug. 1, 1977, Pat. No. 4,123,520.

[51] Int. Cl.$^3$ ............................................. C08B 37/00
[52] U.S. Cl. ........................................ 536/18; 536/1; 424/92; 424/180
[58] Field of Search ............... 424/92, 180, 92; 536/1, 536/18

[56] References Cited

PUBLICATIONS

Kuvakina et al.—Chem. Abst., vol. 81, (1974) p. 134, 317q.
Bhattacharjee et al.—Chem Abst., vol. 84, (1976) p. 134,003W.
Apicella—Chem. Abst., vol. 85, (1976) 92,038Z.

*Primary Examiner*—Johnnie R. Brown
*Assistant Examiner*—Blondel Hazel
*Attorney, Agent, or Firm*—Mario A. Monaco; Donald J. Perrella; Theresa Y. Cheng

[57] ABSTRACT

A vaccine against Group C meningococcal meningitis consisting of a polysaccharide of which at least 80% by weight has a molecular weight in excess of 1,000,000 daltons is prepared. The polysaccharide was isolated from Group C hexadecyl trimethylammonium bromide cell paste with 1.0M $CaCl_2$ extraction and purified by phenol extraction, ultracentrifugation at 100,000 g. and ethanol fractionation (30%–45% v/v in ethanol).

1 Claim, No Drawings

HIGH MOLECULAR WEIGHT MENINGOCOCCAL GROUP C VACCINE AND METHOD FOR PREPARATION THEREOF

This is a division of application Ser. No. 820,665, filed Aug. 1, 1977, now U.S. Pat. No. 4,123,520.

DISCLOSURE OF THE INVENTION

This invention relates to vaccines for immunization against Group C meningococcal meningitis. More particularly, this invention relates to a high molecular weight vaccine that should be effective in inducing immunity against Group C meningococcal meningitis among infants under two years of age. This lower age group is particularly susceptible to infection especially during episodes of epidemic.

Meningococcal meningitis is a disease involving inflammation of the membranes enveloping the brain and spinal cord. In the past, most cases of bacterial meningitis were acute and fatal. The subsequent introduction of antibiotic therapy reduced the mortality rate for cases recognized early in their course. Nonetheless, undiagnosed meningitis remains a morbid disease. Even with antibiotic administration the prognosis is poor especially for the younger patient. This negative prognosis results in part because infants of three months to two years of age rarely manifest typical symptoms of the disease. Thus, antibiotic therapy which must be initiated early is often delayed until the infant is desperately and obviously ill or the presence of the disease is confirmed by laboratory findings.

Meningococcal meningitis is caused by infection by the species *Neisseria meningitides*. This species is classified into serological groups; A, B, C and D etc. Each of these groups is classified by a characteristic capsular polysaccharide associated with the cell wall of that particular group. It was discovered that this cell component comprised of polysaccharide when introduced into a mammal will induce antibody production; hence, protection against later infection.

We have now discovered a process for producing meningococcal polysaccharide vaccines that employ a phenol extraction step for purification of polysaccharide and removal of proteins and that results in vaccine product of higher molecular weight. This is advantageous because it is well accepted that higher molecular weight polysaccharide products achieve a greater level of immunogencity as compared to lower molecular weight material.

This higher molecular weight vaccine was prepared from a culture *Neisseria meningitidis* received through the courtesy of Dr. Emil C. Gotschlich, Rockefeller University. The culture was shown to be a gram-negative diplococcus that is catalase-positive, oxidase-positive and type C with *Neisseria meningitidis* type C antisera. This strain is now deposited with the American Type Culture Collection, Rockville, Maryland 20852 and designated ATCC 31275. It was the above-referred to strain that is employed in the preparative steps set forth in later portions of this specification which detail the preferred mode of practicing this invention. Therefore, it is the preferred strain for vaccine production although others may be equally effective.

The procedures described herein that pertain to the growth of *N. meningitidis* cultures as well as the isolation and purification of the polysaccharide are generally described in Gotschlich, U.S. Pat. No. 3,636,192, especially at columns 3 to 5 inclusive. That patent, and those portions relevant to the above-described aspects and the use of the vaccine of this invention are hereby incorporated by reference into this specification.

A culture of *N. meningitidis* is grown in a suitable manner, but preferably according to the procedure outlined in this specification. Fermentation is terminated and the desired solids containing the polysaccharide is precipitated from the whole culture with a suitable cationic material, for example, a quaternary ammonium salt. Preferably this salt is also bactericidal toward *N. meningitidis*. The salt of choice is hexadecyltrimethyl ammonium bromide. Use of this salt eliminates the need for any pasteurization step. The precipitated fermentation solids are collected by centrifugation and the polysaccharide extracted from the pellet with aqueous calcium chloride.

Ethyl alcohol is added to the combined extractions until the extraction solution is from 25 to 35% v/v in ethanol. The extraction solution is then filtered, and ethanol added to the filtrate until its final concentration is 75-85% v/v. The crude polysaccharide precipitate is then collected by filtration or centrifugation.

This product is either processed immediately or optionally the precipitate of polysaccharide is dried with acetone or other non-miscible liquid for storage.

This crude intermediate polysaccharide is then dissolved in a minimum of a buffered aqueous solution. It is important to maintain the solution of polysaccharide at a pH of 6.8 to 7.2 and any buffer suitable in this range may be used. However, the preferred buffer is aqueous sodium acetate, specifically a solution 0.4 to 0.6 M in sodium acetate. The buffered solution of polysaccharide is then extracted with buffered phenol solution, at least twice and preferably four times. A good buffered phenol solution is one from 70 to 80% w/v in phenol in aqueous buffer that will maintain a pH of 6.8 to 7.2.

The aqueous polysaccharide/phenol mixture is an emulsion, that if broken forms an organic phenol rich layer comprising protein and other debris, an interface and an aqueous polysaccharide rich layer. The phenol layer is disposed of, and the extraction of the aqueous phase is repeated a sufficient number of times to rid the polysaccharide of protein contamination.

A clear aqueous polysaccharide rich phase remains. This is diluted with 0.1 to 0.01 molar calcium chloride until the phenol concentration is below 1% v/v.

The solution is then brought to 30 to 33% v/v of ethanol and ultracentrifuged at 100,000 xg. The clear supernatant fluid is then precipitated by bringing the solution to 40 to 50% v/v in ethanol.

The precipitate is allowed to settle, preferably for at least eight hours at 50° C. The precipitate is collected, washed with an immiscible solvent, and dried under vacuum to give material of which at least 80% has a molecular weight 1,000,000 daltons.

The following specific examples are an illustration of the preferred method of carrying out this invention.

EXAMPLE 1

INOCULUM DEVELOPMENT

STEP 1

Pre-seed Stage

A lyophilized culture tube of *Neisseria meningitidis* ATCC 31275 is opened and suspended in 0.5 ml. of modified Frantz Medium. The composition of this and all other media referred to herein is tabulated in Index I following these examples. The suspension is spread on Mueller-Hinton Medium agar plates (0.1 ml. per plate) and the plates are incubated for 18 hours at 37° C. in a candle jar. The growth from these plates is re-suspended in 3 ml. (per plate) of modified Frantz Medium and spread on Mueller-Hinton plates (0.1 ml. per plate). The plates are incubated for 18 hours at 37° C. in a candle jar. The growth from the second group of plates is re-suspended in Modified Frantz Medium (5 ml. per plate). The pooled suspension is distributed in 2 ml. aliquots into screw cap vials and frozen at −70° C. as pre-seed stock. The pooled suspension is examined microscopically and streaked on Mueller-Hinton plates (25° C. and 37° C.) to establish purity. Serological testing is also performed.

STEP 2

Seed Stage

A pre-seed frozen vial from Step 1 is thawed and 0.1 ml. is spread on Mueller-Hinton plates and incubated for 16 hours at 37° C. in a candle jar. Growth on the plates is suspended (5 ml. per plate) is Modified Frantz Medium. The pooled suspension is examined for purity by streaking on Mueller-Hinton plates (25° C. and 37° C.), microscopic examination and serological identification. The suspension is distributed (2 ml. aliquots) into screw cap vials and frozen at −70° C. as seed stock.

STEP 3

Vegetative State (2 liter)

One frozen vial from the seed stock prepared in Step 2 is thawed and spread on four Mueller-Hinton plates (0.1 ml.–0.15 ml. per plate). The plates are incubated for 16 hours at 37° C. in a candle jar. The growth on each plate is suspended in 5 ml. Modified Frantz Medium and four plates used to inoculate a 2 liter Erlenmeyer flask (containing 1 liter Modified Frantz Medium). The 2 liter flask is incubated for 5 hours at 37° C. on a shaker at 200 RPM. The 1 liter inoculum at time of use has an O.D. of 0.5 and pH 6.4. The 2 liter flask is examined microscopically for purity. The inoculum is streaked on Mueller-Hinton plates incubated for 24 hours (25° C. and 37° C.) and examined for purity.

STEP 4

Inoculum State

One liter of inoculum from Step 3 is used to inoculate a 14 liter New Brunswick Scientific fermentor (MA-100 model) containing 9 liters of fermentation medium. The fermentation is continued for 14 hours at 37° C., 1.5 liters/minute average airflow, and 200 rpm agitation speed. The inoculum at this time has an O.D. of 0.84 and a pH of 5.3. The inoculum is examined microscopically for purity and streaked onto Mueller-Hinton agar plates which are incubated for 24 hours (25° C. and 37° C.) and subsequently examined for purity.

STEP 5

Production Stage

The 10 liters of inoculum from Step 4 is used to inoculate a New Brunswick Scientific fermentor (FM 250 model) containing 190 liters of production medium (see Index). The fermentor is controlled with an airflow of 1 CFM under 1 psi with an average temperature of 37° C. and 200 rpm agitation speed. The fermentation proceeds for 12 hours before termination. The final O.D. is 1.6 and final pH is 5.5. When the fermentation is complete a sample of the culture is examined microscopically by wet mount and gram stain to confirm purity. It is also identified serologically. A sample also is streaked onto Mueller-Hinton agar plates which are incubated (25° C. and 37° C.) for 24 hours and examined for purity.

STEP 6

Harvest and Inactivation Stage

The batch from Step 5 is harvested into 5 gallon jugs containing 10 ml. of 10% Cetavlon (hexadecyltrimethylammonium bromide) per liter of broth and mixed thoroughly. After inactivation, the batch is tested for sterility. Before centrifuging the batch is left at least two hours with Cetavlon to insure a good precipitation.

INDEX OF FERMENTATION MEDIA

Seed Medium a. Mueller-Hinton Agar
  1. Dehydrated Difco Mueller-Hinton Medium agar 40 gms. per liter.
b. Modified Frantz-2 liter flasks
  Casamino Acids (Certified): 300 gms.
  Dextrose: 150 gms.
  $Na_2HPO_4$ Anhydrous: 82.5 gms.
  $MgSO_4.7H_2O$: 19.5 gms.
  KCl: 2.75 gms.
  L-Cysteine HCl monohydrate: 605 mg.
  Phenol Red: 99 mg.
  Distilled $H_2O$: 30 liters
This medium is sterilized by filtration through a Millipore filter (0.22 micron) and dispensed aseptically 1 liter/2 liter Erlenmeyer flask.
c. Inoculum Medium-14 Liter Fermentor
  The following was added to the fermentor and sterilized for 60 minutes at 121° C.:
  UCON LB625 lubricant 8%: 10 ml.
  Phenol red: 30 mg.
  $Na_2HPO_4$: 27.5 gm.
  Distilled $H_2O$: 8 liters
The LB625 lubricant was pre-sterilized for 60 minutes at 121° C. before addition to the fermentor.
  The following concentrate was filtere-sterilized into the sterile fermentor:
  Casamino Acids (Technical): 100 gms.
  Dextrose: 50 gms.
  $MgSO_4.7H_2O$: 6.5 gms.
  KCl: 917 mg.
  L-Cysteine HCl monohydrate: 201.8 mg.
  Distilled $H_2O$: 1 liter
A 293 mm. (0.22 micorn) Millipore was used as the filter.

Fermentation Medium

The following was added to the fermentor and sterilized for 30 minutes at 121° C.:
  400 ml. of 8% UCON LB625 lubricant
  634 mg. Phenol Red
  530 gm. $Na_2HPO_4$
  170 liters distilled $H_2O$
The LB625 lubricant was pre-sterilized for 60 minutes at 121° C. before addition to the fermentor.
  The following concentrate was filter-sterilized into the sterile fermentor:
  Casamino Acids (Technical): 2700 gms.
  Glucose: 1080 gms.

$MgSO_4.7H_2O$: 140.4 gms.
KCl: 19.8 gms.
L-Cysteine HCl monohydrate: 4.4 gms.
Distilled $H_2O$: 20 liters A Horn Press using D-8 filter pads was used as a pre-filter and a 293 mm. (0.22 micron) Millipore used as the final filter.

INDEX II

Inactivation Procedure

After initial contact with Cetavlon the minimum contact time was two hours. The batch was then tested for sterility as described in INDEX III.

INDEX III

Sterility Test for Inactivation

A 0.5 ml. aliquot portion of the solution to be tested in spread on a Mueller-Hinton plate and incubated in a candle jar at 37° C. for 18 hours. A positive sterility test is obtained when the plates are examined microscopically at 10× magnification and no microbial growth is observed.

INDEX IV

Macroscopic Slide Agglutination Test (Serological Test)

A drop of rehydrated Bacto-Meningococcus Antiserum (Type C) is placed on a slide. A loopful of *N. meningococcus* growth is then transferred to the drop of antiserum and mixed with the antiserum. A positive test is observed when an agglutination of the cells occurs.

EXAMPLE II

THE PREPARATION OF HIGH MOLECULAR WEIGHT VACCINE

Following the addition of Cetavlon (hexadecyltrimethylammonium bromide) to a level of 0.1% v/v, 2.24 kg. of wet fermentation solids are obtained from 600 liters of a non-pasteurized culture of *N. meningiditis* Group C by centrifugation in a 4" diameter tubular bowl Sharples centrifuge.

The fermentation solids are washed by homogenizing in an 8 gallon dispersion mixer with 20 liters pyrogen free water. The washed solids are collected by centrifugation in a 4" diameter tubular bowl Sharples centrifuge.

The polysaccharide is extracted from the resultant 2.0 KG. washed paste by homogenizing in an 8 gallon dispersion mixer with 15 liters ionic calcium chloride solution. Anhydrous ethyl alcohol is added to this slurry to level of 33% ethanol v/v, and a clear supernatant is obtained by centrifugation at 12,000 XG. in clinical refrigerated centrifuges for 30 minutes at −5° C.−10° C. The supernatant is further clarified by filtration through a 670 $CM^2$ medium porosity pressure filter.

The filtrate is added to ethanol, calculated to give a final concentration of 80% ethanol v/v, while agitated in a 30 gallon stainless steel kettle. The resulting crude polysaccharide precipitate is collected using a 2" diameter sharples centrifuge. The solids are homogenized in a 1 quart Waring Blender with 500 ml acetone and collected in a clinical centrifuge at 12,000 XG. for ten minutes. 500.4 Gms. of acetone wet precipitate are obtained.

250.2 Gms. of the crude intermediate is dissolved in 12.8 liters of a 0.48 M sodium acetate buffer pH 6.9, using an 8 gallon dispersion mixer. This solution is mixed with 4.48 liters of a phenol solution made by adding 900 ml. of the sodium acetate buffer to 2.27 Kg. of crystalline phenol. The emulsion is then fed to continuous electronucleonics "K" ultracentrifuge at a flow rate of 300 ml./min. at 30,000 rpm. Insoluble phenol and interfacial material remains in the spinning bowl while deprotenized supernatant liquid overflows and is collected. The phenol layer is discarded and phenol saturated supernatant is mixed with 3.2 liters phenol solution for another extraction. A total of four phenol extractions are carried out on the polysaccharide solution, to give 15.2 liters of a clear aqueous phase. The remaining 250.2 gms. crude intermediate is extracted with phenol as above to give 15.6 liters of a clear aqueous phase.

Each of the aqueous phases are diluted 20 fold (300 liters) with 0.05 M calcium chloride solution to a phenol concentration of below 0.5% v./v. The solutions were each concentrated to 15 liters using an Amicon hollow fiber ultrafiltration apparatus employing 10,000 molecular weight cut off membranes. Phenol and small molecular weight material are further removed by constant retentate volume ultrafiltration (Diafiltration) to collect an additional 30 liters permeate.

The retentate fractions from both halves are combined in a 30 gallon stainless steel kettle and brought to 30% v./v. by the addition of anhydrous ethanol, with agitation. This solution is ultracentrifuged by feeding it to an electronucleonics K-ultracentrifuge at a rate of 200 ml./min. and 30,000 rpm. The clarified supernatant is then added to a 30 gallon stainless steel kettle and brought to 40–45% v./v. ethanol by addition with agitation. The precipitate was allowed to settle 18 hours at 5° C.

The sticky adhering precipitate is dissolved from the kettle walls with 2 liters 0.02 M calcium chloride. This solution is added to 4 liters anhydrous ethanol and the precipitate collected by centrifugation at 12,000 XG for 10 minutes. The solids are washed twice in 500 ml. acetone by homogenizing in a Waring Blender followed by collection by centrifugation at 12.000 XG for 10 minutes. The final purified polysaccharide is dried under vacuum at 5° C. for 72 hours to give 32.9 gms. Final quality assays are:

Protein %: 0.33
Nucleic Acid %: 0.08
Sialic Acid %: 85.2
Moisture %: 15.2
O-Acetyl: 2.21 μm/mg.
Rabbit Pyrogen:
Temperature Rise at 0.025 micro gm./kg. Body Weight, respectively: 0.0, 0.0, 0.2
Sepharose 4B Kd: 0.2
% Sialic Recovered before Kd 0.40: 86.1
Hemo Agglutenation Inhibition: 400.

What is claimed is:

1. An antigen meningococcal polysaccharide active against Group C meningococci wherein at least 80% of the polysaccharide by weight has a molecular weight in excess of 1,000,000 daltons.

* * * * *